(12) United States Patent
Hazin et al.

(10) Patent No.: US 12,727,782 B2
(45) Date of Patent: Sep. 8, 2026

(54) SYSTEMS, DEVICES, AND METHODS FOR WIRELESS POWER TRANSFER FROM POWER SOURCE SYSTEM TO MEDICAL IMPLANT

(71) Applicant: Howmedica Osteonics Corp., Mahwah, NJ (US)

(72) Inventors: Wael Hazin, Plantation, FL (US); Matthias Verstraete, Chaam (NL); Ezra Johnson, Reeds Springs, MO (US); Carlos Alva, Boynton Beach, FL (US)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 378 days.

(21) Appl. No.: 18/505,448

(22) Filed: Nov. 9, 2023

(65) Prior Publication Data

US 2024/0156367 A1 May 16, 2024

Related U.S. Application Data

(60) Provisional application No. 63/383,278, filed on Nov. 11, 2022.

(51) Int. Cl.
*A61B 5/103* (2006.01)
*A61B 5/00* (2006.01)
*H02J 50/12* (2016.01)

(52) U.S. Cl.
CPC .......... *A61B 5/1036* (2013.01); *A61B 5/0031* (2013.01); *A61B 5/6878* (2013.01); *H02J 50/12* (2016.02); *A61B 2560/0219* (2013.01)

(58) Field of Classification Search
CPC ... A61B 5/1036; A61B 5/0031; A61B 5/6878; A61B 2560/0219; H02J 50/12; H02J 50/80

(Continued)

(56) References Cited

U.S. PATENT DOCUMENTS 9,384,885 B2 * 7/2016 Karalis .................. H02J 50/80
9,564,777 B2 * 2/2017 Yeh ........................ A61B 18/18

(Continued)

FOREIGN PATENT DOCUMENTS

WO 2021081426 A1 4/2021

OTHER PUBLICATIONS

Sid Assawwarrarit et al."Robust and efficient wireless power transfer using a switch-mode implementation of a nonlinear parity-time symmetric circuit", nature electronics Articles, https://doi.org/10.1038/s41928-020-0399-7, (7 paes).

*Primary Examiner* — Eric Blount
(74) *Attorney, Agent, or Firm* — Bookoff McAndrews, PLLC

(57) ABSTRACT

A wirelessly powered medical implant system comprising: a power source system including: an automatic gain controller to receive input power, automatically adjust the input power based on a feedback signal with an offset phase delay, and provide the adjusted input power as output power; a source resonator to generate, based on the output power, a magnetic field to transmit wireless power via the magnetic field, and provide the feedback signal; and an offset phase delay circuit to receive the feedback signal from the source resonator, generate the offset phase delay, and include the offset phase delay with the feedback signal; and a medical implant including: an implant resonator to receive the transmitted wireless power via the magnetic field; and one or more sensors, wherein the feedback signal is based on inductive coupling of the magnetic field between the source resonator and the implant resonator.

20 Claims, 6 Drawing Sheets

(58) Field of Classification Search
USPC ..................................................... 340/539.12
See application file for complete search history.

(56) References Cited

U.S. PATENT DOCUMENTS

| | | | | |
|---|---|---|---|---|
| 10,348,139 | B2 * | 7/2019 | Piasecki .................. | H02J 50/60 |
| 11,653,880 | B2 * | 5/2023 | Felix .................... | A61B 5/0006 600/515 |
| 12,155,227 | B2 * | 11/2024 | Assawaworrarit ...... | H02J 50/05 |
| 12,592,590 | B2 * | 3/2026 | Kasireddy ............... | H02J 50/80 |
| 2009/0058361 | A1 * | 3/2009 | John ....................... | H02J 50/80 307/104 |
| 2013/0033118 | A1 * | 2/2013 | Karalis ................. | B60L 53/126 307/104 |
| 2013/0215979 | A1 * | 8/2013 | Yakovlev ................. | H04B 5/79 375/256 |
| 2018/0241252 | A1 * | 8/2018 | Fan .......................... | H04B 5/79 |
| 2020/0046986 | A1 * | 2/2020 | Chang .................. | A61N 1/3787 |
| 2021/0384771 | A1 * | 12/2021 | Hansen ................... | H01F 38/14 |
| 2022/0385107 | A1 * | 12/2022 | Assawaworrarit ...... | H02J 50/40 |

* cited by examiner

SYSTEMS, DEVICES, AND METHODS FOR WIRELESS POWER TRANSFER FROM POWER SOURCE SYSTEM TO MEDICAL IMPLANT

CROSS-REFERENCE TO RELATED APPLICATIONS

This application claim the benefit of priority to U.S. Provisional Patent Application No. 63/383,278, filed Nov. 11, 2022, which is incorporated by reference herein in its entirety.

TECHNICAL FIELD

Various embodiments of the present disclosure relate generally to systems, devices, and methods for wireless power transfer from a power source system to a medical implant, and, more particularly, to systems, devices, and methods for wireless power transfer with feedback control from a power source system to a medical implant.

BACKGROUND

Current wireless power transfer systems using magnetic-field coupling rely heavily on predetermined transfer distances between a power source system and a receiving device and/or limited variability of an ideal design distance. This approach does not apply well for medical implant use because of a great variability of tissue depth among patients.

The present disclosure is directed to overcoming one or more of these above-referenced challenges.

SUMMARY OF THE DISCLOSURE

In some aspects, the techniques described herein relate to a wirelessly powered medical implant system including: a power source system including: an automatic gain controller to receive input power, automatically adjust the input power based on a feedback signal with an offset phase delay, and provide the adjusted input power as output power; a source resonator to generate, based on the output power, a magnetic field to transmit wireless power via the magnetic field, and provide the feedback signal; and an offset phase delay circuit to receive the feedback signal from the source resonator, generate the offset phase delay, and include the offset phase delay with the feedback signal, wherein the automatic gain controller is configured to increase a signal-to-noise ratio of the feedback signal with the offset phase delay from the offset phase delay circuit and decrease a phase shift of a switching signal to the source resonator; and a medical implant including: an implant resonator to receive the transmitted wireless power via the magnetic field; and one or more sensors to respond to a stimulus of the medical implant using the received power, wherein the feedback signal is based on inductive coupling of the magnetic field between the source resonator and the implant resonator.

In some aspects, the techniques described herein relate to a system, wherein the automatic gain controller includes: a variable gain amplifier including an input electrically connected to an output of the offset phase delay circuit to receive the feedback signal with the offset phase delay.

In some aspects, the techniques described herein relate to a system, wherein the automatic gain controller further includes: a second stage amplifier including an input electrically connected to an output of the variable gain amplifier, and an output to provide the switching signal to the source resonator.

In some aspects, the techniques described herein relate to a system, wherein the automatic gain controller further includes: a feedback integrator including an input electrically connected to an output of the second stage amplifier, and an output to provide a signal to the variable gain amplifier.

In some aspects, the techniques described herein relate to a system, wherein the automatic gain controller further includes: a servo integrator including an input electrically connected to an output of the second stage amplifier, and an output to provide a signal to the variable gain amplifier.

In some aspects, the techniques described herein relate to a system, wherein the automatic gain controller automatically adjusts the input power based on the feedback signal with the offset phase delay using parity time symmetry, and wherein the feedback signal is a coupling rate between the source resonator and the implant resonator.

In some aspects, the techniques described herein relate to a system, wherein the offset phase delay circuit includes a resistor and capacitor in parallel to generate the offset phase delay.

In some aspects, the techniques described herein relate to a system, wherein the medical implant is a knee implant, and the stimulus to the one or more sensors is one or more of a location or a magnitude of a load, or a change in the same of the one or more sensors of the knee implant.

In some aspects, the techniques described herein relate to a wirelessly powered medical implant system including: a power source system including: an automatic gain controller to receive input power, automatically adjust the input power based on a feedback signal with an offset phase delay, and provide the adjusted input power as output power; a source resonator to generate, based on the output power, a magnetic field to transmit wireless power via the magnetic field, and provide the feedback signal; an offset phase delay circuit to receive the feedback signal from the source resonator, generate the offset phase delay, and include the offset phase delay with the feedback signal; and a source controller to control the input power based on a power signal to limit the received power based on a threshold; and a medical implant including: an implant resonator to receive the transmitted wireless power via the magnetic field; and one or more sensors to respond to a stimulus of the medical implant using the received power, wherein the feedback signal is based on inductive coupling of the magnetic field between the source resonator and the implant resonator.

In some aspects, the techniques described herein relate to a system, wherein the power source system further includes a source transceiver to receive the power signal from the medical implant.

In some aspects, the techniques described herein relate to a system, wherein the medical implant further includes: an implant transceiver to send the power signal to the power source system based on an amount of the wireless power received by the medical implant via the magnetic field.

In some aspects, the techniques described herein relate to a system, wherein the power signal provides information to the power source system that causes the source controller to control the input power to minimize heat in the medical implant due to excess wireless power received by the medical implant.

In some aspects, the techniques described herein relate to a system, wherein the medical implant further includes an AC to DC rectifier to convert the received power to DC power.

In some aspects, the techniques described herein relate to a system, wherein the medical implant is a knee implant, and the stimulus to the one or more sensors is one or more of a location or a magnitude of a load, or a change in the same of the one or more sensors of the knee implant.

In some aspects, the techniques described herein relate to a wirelessly powered medical implant system including: a power source system including: an automatic gain controller to receive input power, automatically adjust the input power based on a feedback signal with an offset phase delay, and provide the adjusted input power as output power; a source resonator to generate, based on the output power, a magnetic field to transmit wireless power via the magnetic field, and provide the feedback signal, wherein the source resonator includes: a resonant tank circuit, a switch to drive the resonant tank circuit, and a switch protector to limit power to the switch; and an offset phase delay circuit to receive the feedback signal from the source resonator, generate the offset phase delay, and include the offset phase delay with the feedback signal; and a medical implant including: an implant resonator to receive the transmitted wireless power via the magnetic field; and one or more sensors to respond to a stimulus of the medical implant using the received power, wherein the feedback signal is based on inductive coupling of the magnetic field between the source resonator and the implant resonator.

In some aspects, the techniques described herein relate to a system, wherein the source resonator further includes: a driver comparator to receive the output power from the automatic gain controller, compare the output power with a power reference signal, and output a driver signal based on the comparison of the output power with the power reference signal.

In some aspects, the techniques described herein relate to a system, wherein the switch protector includes: a protection comparator to receive an output signal from the resonant tank circuit of the source resonator, compare the output signal with a protection reference signal, and output a switch protection signal based on the comparison of the output signal with the protection reference signal.

In some aspects, the techniques described herein relate to a system, wherein the driver comparator receives the switch protection signal, and outputs the driver signal based on both (1) the comparison of the output power with the power reference signal, and (2) the protection reference signal.

In some aspects, the techniques described herein relate to a system, wherein the driver comparator includes a latch input, and the switch protection signal is received by the latch input.

In some aspects, the techniques described herein relate to a system, wherein the medical implant is a knee implant, and the stimulus to the one or more sensors is one or more of a location or a magnitude of a load, or a change in the same of the one or more sensors of the knee implant.

As will be apparent from the embodiments below, the disclosed systems and methods may provide, for example, a constant wireless power transfer efficiency for a wide range of transfer distances without the need for external tuning. The disclosed systems and methods discussed below may also help reduce electromagnetic field exposure to a patient, reduce a potential temperature rise of an implant in a body of a patient, reduce a power supply volume and/or weight of the power source system, reduce electronic component temperature rise of the power source system and medical implant, and reduce an implant charging time.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Both the foregoing general description and the following detailed description are exemplary and explanatory only and are not restrictive of the features, as claimed. As used herein, the terms "comprises," "comprising," "having," "including," or other variations thereof, are intended to cover a non-exclusive inclusion such that a process, method, article, or apparatus that comprises, has, or includes a list of elements does not include only those elements, but may include other elements not expressly listed or inherent to such a process, method, article, or apparatus. In this disclosure, relative terms, such as, for example, "about," substantially," "generally," and "approximately" are used to indicate a possible variation of ±10% in the stated value. The term "exemplary" is used in the sense of "example" rather than "ideal." As used herein, the singular forms "a," "an," and "the" include plural reference unless the context dictates otherwise.

Figure 1:
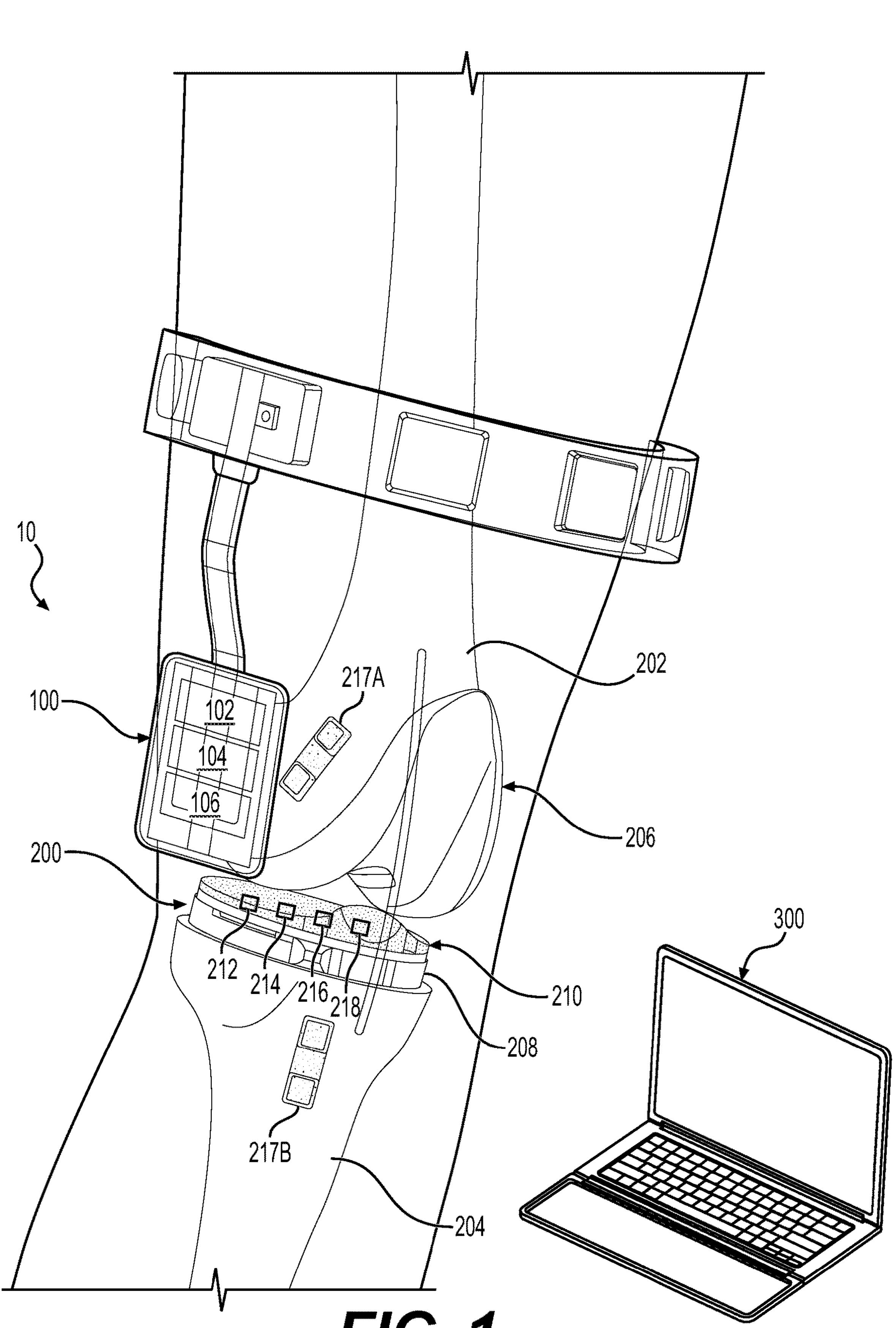
FIG. 1 depicts an exemplary system for wireless power transfer from a power source system to a medical implant.

FIG. 1 depicts an exemplary system for wireless power transfer from a power source system to a medical implant. As shown in FIG. 1, wirelessly powered medical implant system 10 may include power source system 100, medical implant 200, and user interface 300. While wirelessly powered medical implant system 10 will be described below in the context of a medical knee implant, the system may alternatively be implemented in other implants for a patient's body, such as, for example, implants for a patient's back, shoulder, spine, or hip. However, the embodiments are not limited thereto.

Power source system 100 may be worn on a patient's leg, for example, and provide power to medical implant 200. Power source system 100 may include source power 102 to provide power to power source system 100, source controller 104 to control power source system 100, and source transmitter 106 to wirelessly deliver power to medical implant 200.

Medical implant 200 may be implanted in a patient's knee, for example. Medical implant 200 may include femoral prosthetic component 206 and femoral magnetic component 217A, both connected to a patient's femur 202.

Medical implant 200 may include tibial prosthetic component 208 and tibial magnetic component 217B, both connected to a patient's tibia 204. Medical implant 200 may include a medical insert 210 provided between femoral prosthetic component 206 and tibial prosthetic component 208. Medical insert 210 may include implant power system 212 to provide power to medical implant 200, implant controller 214 to control medical implant 200, one or more sensors 216 to sense aspects of the medical implant, such as a location of femoral magnetic component 217A and tibial magnetic component 217B, and implant receiver 218 to wirelessly receive power from power source system 100 for implant power system 212. While one or more sensors 216 are shown as location or position type sensors, one or more sensors 216 could be any type of sensors, such as one or more sensors measuring a location and/or magnitude of load, or a change in the same.

User interface 300 may be a computer in wireless communication with medical implant 200 to receive measurement data from one or more of power source system 100 or medical implant 200 to process and display information related to the patient's femur 202 and tibia 204. User interface 300 may be placed in proximity to one or more of power source system 100 or medical implant 200. User interface 300 may receive measurement data (e.g. measured by one or more sensors 216) from one or more of power source system 100 or medical implant 200 via wireless transmission. User interface 300 may include a computer with a display to receive and process measurement data from one or more of power source system 100 or medical implant 200. User interface 300 may include software programs to support calculation and visualization of the measurement data. User interface 300 may be a microprocessor-based device capable of running software, such as, for example, a smart phone or handheld device that allows a patient or other user to review measurement data transmitted from one or more of power source system 100 or medical implant 200.

Figure 2:
FIG. 2 depicts a detailed view of the exemplary system of FIG. 1.

FIG. 2 depicts a detailed view of the exemplary system of FIG. 1. Medical insert 210 may include housing 220. Housing 220 may include at least one cavity for implant power system 212, implant controller 214, one or more sensors 216, and implant receiver 218. Housing 220 may include surfaces that may be coupled together via an adhesive that seals the cavity from the external environment. The interior and exterior of housing 220 may be sterilized and stored in a package prior to use. As shown, the implant receiver 218 may be located on a top, front surface of housing 220. Implant power system 212 and implant controller 214 may be centrally located internally within medical insert 210. The one or more sensors 216 may be located on side portions of the implant power system 212 and/or implant controller 214, and be within or adjacent opposing wing portions of the medical insert 210.

Figure 3:
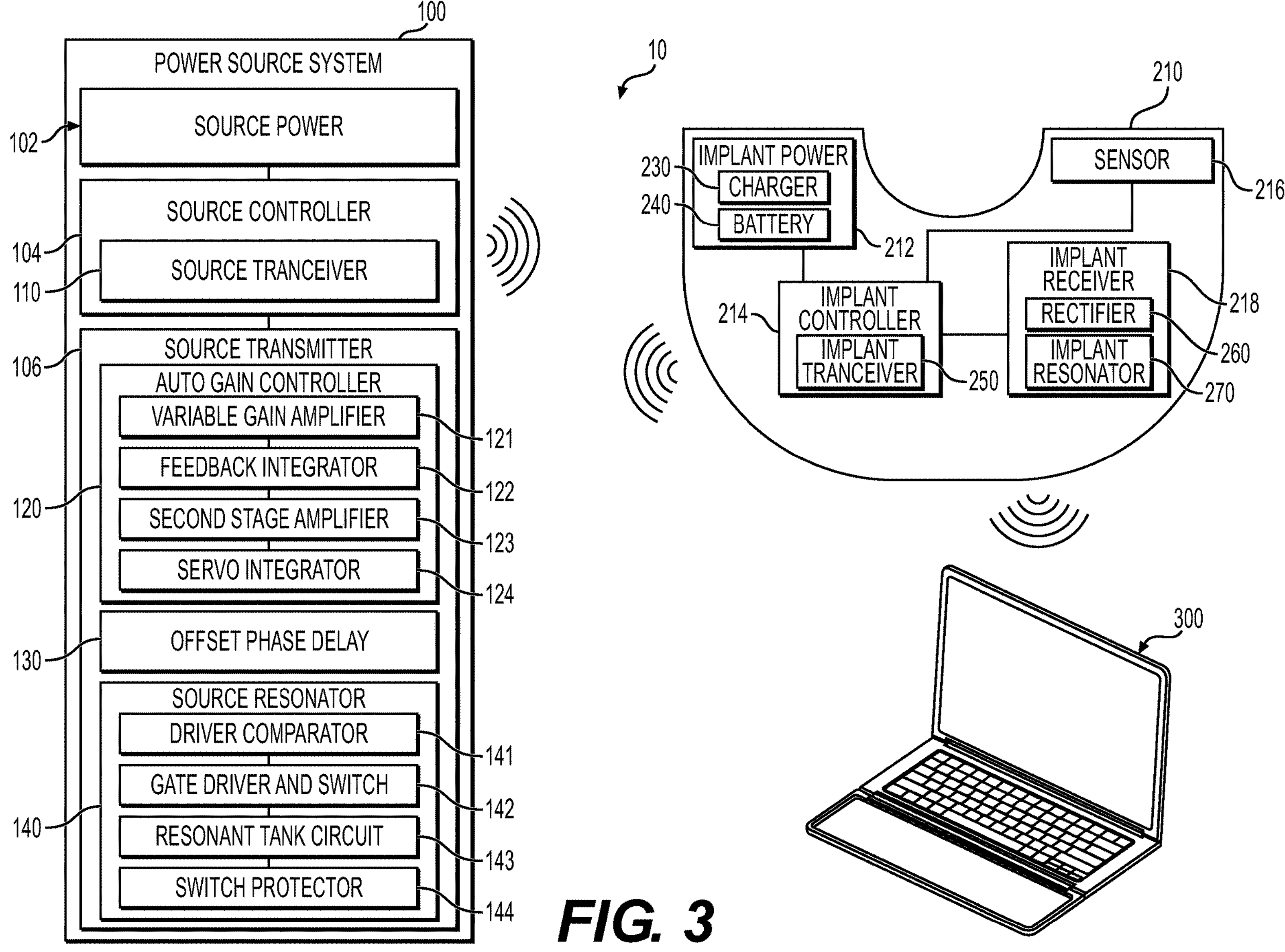
FIG. 3 depicts a functional block diagram of the exemplary system of FIG. 1.

FIG. 3 depicts a functional block diagram of the exemplary system of FIG. 1. As shown in FIG. 3, wirelessly powered medical implant system 10 may provide wireless power transfer from power source system 100 to medical implant 200 including medical insert 210, and medical implant 200 including medical insert 210 may communicate with user interface 300.

Power source system 100 may include source power 102 to provide power to power source system 100, source controller 104 to control power source system 100, and source transmitter 106 to wirelessly deliver power to medical implant 200.

Source power 102 may include one or more batteries or power cords to store or directly deliver electric power to the components of power source system 100. Source controller 104 may receive power from source power 102. Source controller 104 may include one or more processors to control a transmission of power to medical implant 200, and may include source transceiver 110 to send and receive data from one or more of medical implant 200 or user interface 300. Source transmitter 106 may include automatic gain controller 120 to automatically adjust a gain, offset phase delay circuit 130 to provide a feedback signal to automatic gain controller 120, and source resonator 140 to send wireless power based on the adjusted gain.

Automatic gain controller 120 may include variable gain amplifier 121, feedback integrator 122, second stage amplifier 123, and servo integrator 124. Source resonator 140 may include driver comparator 141, gate driver and switch 142, resonant tank circuit 143, and switch protector 144.

Medical insert 210 may include implant power system 212, implant controller 214, one or more sensors 216, and implant receiver 218 to receive wireless power and convert the received power for use by medical implant 200, such as to charge battery 240, for example. Implant power system 212 may include battery 240 to provide operating power for medical implant 200, and charger 230 to control power delivered to battery 240. Battery 240 may be any short-term, long-term power, and/or rechargeable storage and delivery element. Implant controller 214 may include one or more processors to control the reception of wireless power, and may include implant transceiver 250 to send and receive data from one or more of power source system 100 or user interface 300. Implant receiver 218 may include implant resonator 270 to receive wireless power from power source system 100, and rectifier 260 to convert the received AC power from implant resonator 270 to DC power for use by medical implant 200.

As stated above, source controller 104 of power source system 100 may include one or more processors to control a transmission of power to medical implant 200, and may include source transceiver 110 to receive data from medical implant 200. Source controller 104 may control input power to source transmitter 106 based on a power signal received by source transceiver 110 from medical implant 200 to limit the power received by medical implant 200 based on a threshold. Here, limiting the power may refer to decreasing the power received by medical implant 200 by any amount greater than 0% and less than or equal to 100%. For example, when battery 240 is completely charged, the power signal received by source transceiver 110 from medical implant 200 may cause the power received by medical implant 200 to be decreased so that no additional power is received by medical implant 200 while battery 240 is above a charge threshold. As another example, when a heat measurement during a charging operation indicates the battery 240 is above, or is trending to be above, a threshold temperature based on power being received by medical implant 200, the power signal received by source transceiver 110 from medical implant 200 may cause the power received by medical implant 200 to be decreased by 10% to lower an actual or expected temperature of battery 240.

As stated above, implant controller 214 of medical implant 200 may include one or more processors to control the reception of wireless power, and may include implant transceiver 250 to send data to power source system 100. Implant controller 214 may control implant transceiver 250 to send the power signal to source transceiver 110 based on an amount of wireless power received by medical implant 200 via the magnetic field. The power signal may provide information to the source controller 104 that causes the source controller 104 to control the input power to source transmitter 106 to minimize heat in the medical implant 200 due to excess wireless power received by medical implant 200. Reducing the excess wireless power received by medical implant 200 based on a threshold may reduce electronic component temperature rise of the power source system 100 and medical implant 200, and thus help avoid detrimental or undesired high temperatures of the source system 100 and/or medical implant 200 in a body of a patient.

Figure 4:
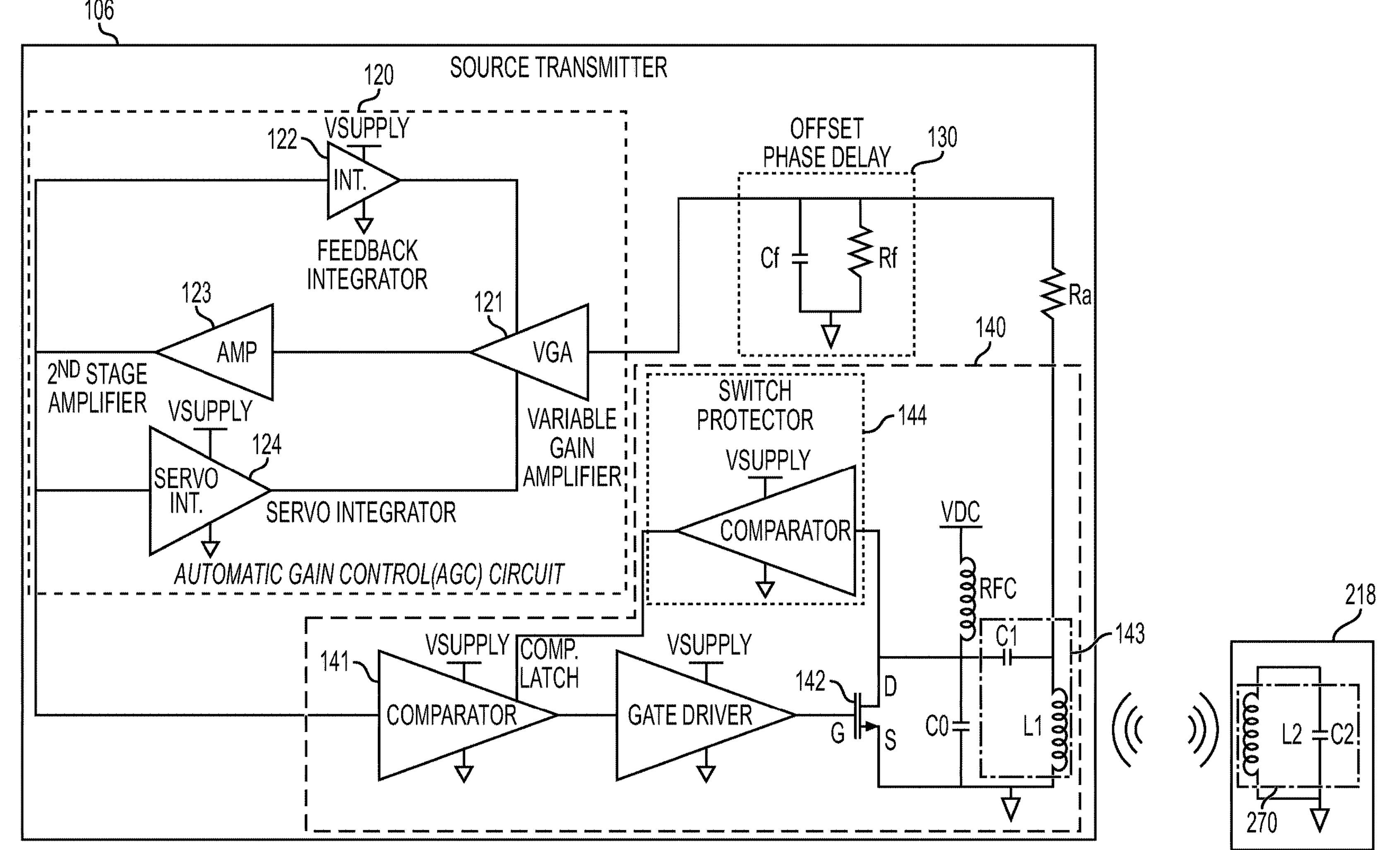
FIG. 4 depicts an exemplary electrical block diagram of the source transmitter and implant receiver of the exemplary system of FIG. 1.

FIG. 4 depicts an exemplary electrical block diagram of the source transmitter 106 and implant receiver 218 of the exemplary system of FIG. 1. As shown in FIG. 4, source transmitter 106 of power source system 100 may wirelessly deliver power to implant receiver 218 of medical implant 200.

Source transmitter 106 may include automatic gain controller 120, offset phase delay circuit 130, and source resonator 140. Automatic gain controller 120 may include variable gain amplifier 121, feedback integrator 122, second stage amplifier 123, and servo integrator 124. Offset phase delay circuit 130 may include resistor Rf and capacitor Cf in parallel to generate an offset phase delay. Capacitor Cf may be used instead of an inductor to reduce a size of source transmitter 106 and power source system 100. Source resonator 140 may include driver comparator 141, gate driver and switch 142, resonant tank circuit 143, and switch protector 144. Source transmitter 106 may include various other components such as inductor RFC, capacitor CO, and resistor Ra, for example. Resistor Ra may attenuate a feedback signal from source resonator 140.

Implant receiver 218 of medical implant 200 may include implant resonator 270 including inductor L2 and capacitor C2 to receive wireless power from resonant tank circuit 143 of source transmitter 106 of power source system 100.

Automatic gain controller 120 may receive input power, automatically adjust the input power based on a feedback signal with an offset phase delay, and provide the adjusted input power as output power. Source resonator 140 may generate, based on the output power, a magnetic field to transmit wireless power via the magnetic field, and provide the feedback signal. Offset phase delay circuit 130 may receive the feedback signal from source resonator 140, generate the offset phase delay, and include the offset phase delay with the feedback signal. Automatic gain controller 120 may increase a signal-to-noise ratio of the feedback signal with the offset phase delay from offset phase delay circuit 130 and decrease a phase shift of a switching signal to source resonator 140. Accordingly, the efficiency of the switching signal may be increased by switching independently of an amplitude of the feedback signal and minimizing power loss from overlapping voltage and current.

The function of the automatic gain controller 120 may be to ensure the input into the comparator 141 is constant in amplitude. The servo integrator 124 compensates for the automatic gain controller 120 output offset. The combination of these two functions may ensure that a varying amplitude of the feedback signal does not create any unwanted variation in phase shift in a signal from the comparator 141. The combination of these two functions may increase the signal-to-noise ratio of the feedback signal because an amplitude of the feedback signal may be much greater than any circuit noise. As an example, if the attenuated feedback signal when the required transfer power is low has an amplitude of 25 mV (RMS), the signal-to-noise ratio of the feedback signal may be 25 mV/circuit noise. Comparing this signal-to-noise ratio to an amplified feedback signal from automatic gain controller 120 of 2.5 V may yield an increased signal-to-noise ratio 100 times larger than the signal-to-noise ratio of the attenuated feedback signal.

Implant resonator 270 may receive the transmitted wireless power via the magnetic field. The feedback signal may be based on inductive coupling of the magnetic field between the source resonator 140, including resonant tank circuit 143, and the implant resonator 270.

Automatic gain controller 120 may include a variable gain amplifier 121 including an input electrically connected to an output of the offset phase delay circuit 130 to receive the feedback signal with the offset phase delay. Automatic gain controller 120 may include a second stage amplifier 123 including an input electrically connected to an output of the variable gain amplifier 121, and an output to provide the switching signal to the source resonator 140. Automatic gain controller 120 may include a feedback integrator 122 including an input electrically connected to an output of the second stage amplifier 123, and an output to provide a signal to the variable gain amplifier 121. Automatic gain controller 120 may include a servo integrator 124 including an input electrically connected to an output of the second stage amplifier 123, and an output to provide a signal to the variable gain amplifier 121.

Variable gain amplifier 121 may vary a gain of the feedback signal based on signals from feedback integrator 122 and servo integrator 124. Feedback integrator 122 may integrate a signal from second stage amplifier 123. Second stage amplifier 123 may increase a gain of a signal from variable gain amplifier 121. Servo integrator 124 may integrate a signal from second stage amplifier 123 to compensate for, or reduce, an offset of the automatic gain controller 120.

Automatic gain controller 120 may automatically adjust the input power based on the feedback signal with the offset phase delay using parity time symmetry models for power source system 100 and medical implant 200. The feedback signal may be a coupling rate between the source resonator 140 and the implant resonator 270. The feedback signal with the offset phase delay may provide a constant wireless power transfer efficiency for a wide range of transfer distances without the need for external tuning, and may reduce charging time of medical implant 200.

Source transmitter 106 may include source resonator 140, which may generate, based on the output power, a magnetic field to transmit wireless power via the magnetic field, and provide the feedback signal. The source resonator 140 may include a resonant tank circuit 143, a gate driver and switch 142 to drive the resonant tank circuit 143, a driver comparator 141 to drive the gate driver and switch 142, and a switch protector 144 to limit power to, and therefore current through, the switch 142.

Source transmitter 106 may include an offset phase delay circuit 130 to receive the feedback signal from the source resonator 140, generate the offset phase delay, and include the offset phase delay with the feedback signal.

Source resonator 140 may include a driver comparator 141 to receive the output power from the automatic gain controller 120, compare the output power with a power reference signal, and output a driver signal based on the comparison of the output power with the power reference signal. Switch protector 144 may include a protection comparator to receive an output signal from the resonant tank circuit 143 of the source resonator 140, compare the output signal with a protection reference signal, and output a switch protection signal based on the comparison of the output signal with the protection reference signal to limit a duration of the switch 142 in an on (current-passing) state.

Driver comparator 141 may receive the switch protection signal, and output the driver signal based on both (1) the comparison of the output power with the power reference signal, and (2) the protection reference signal. Driver comparator 141 may include a latch input, and the switch protection signal may be received by the latch input. Accordingly, the gate driver and switch 142 may be turned on only when the power is below a safe level for the gate driver and switch 142.

Figure 5:
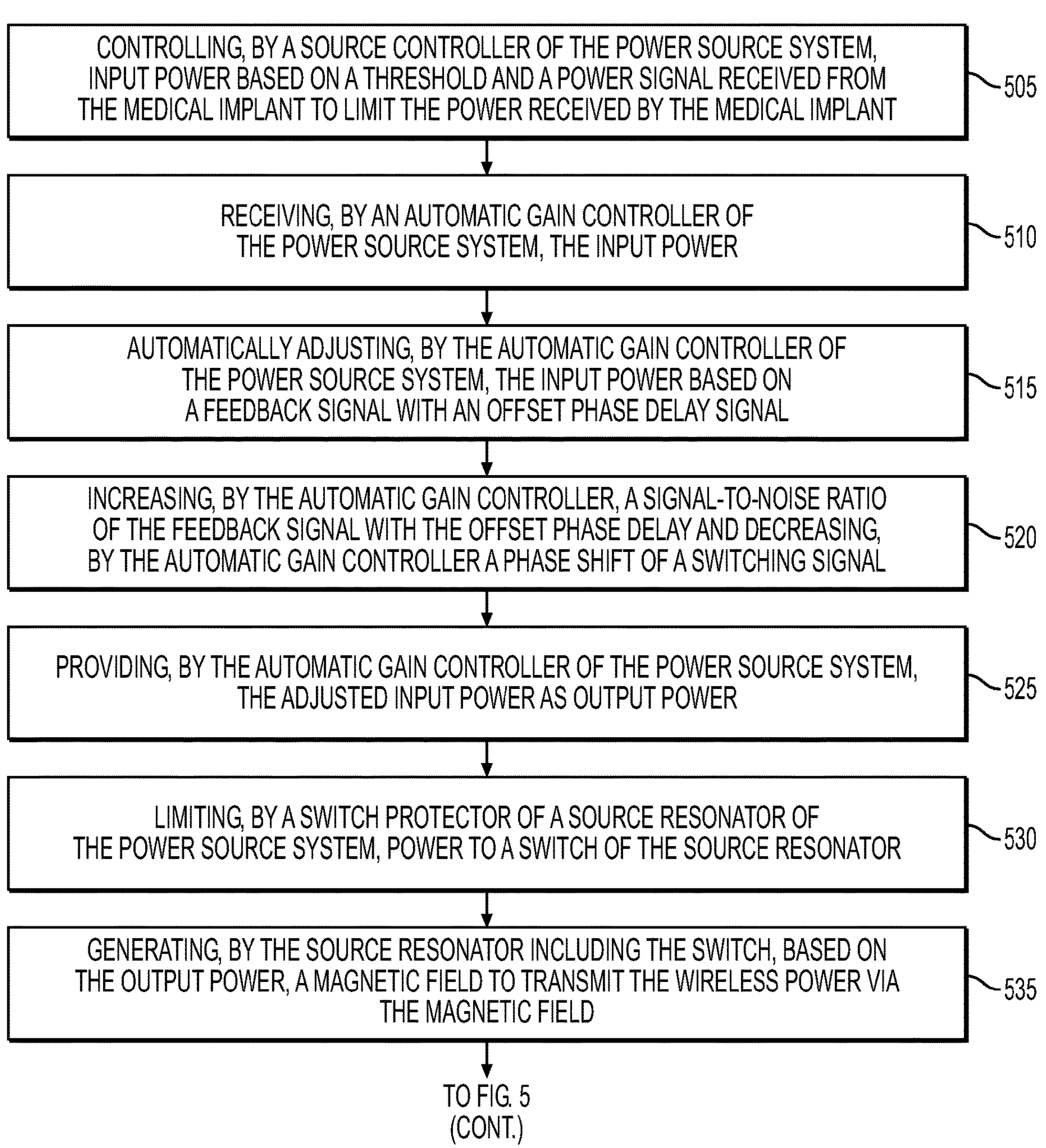
FIG. 5 depicts a flowchart of a method for wireless power transfer using the exemplary system of FIG. 1.
Figure 5:
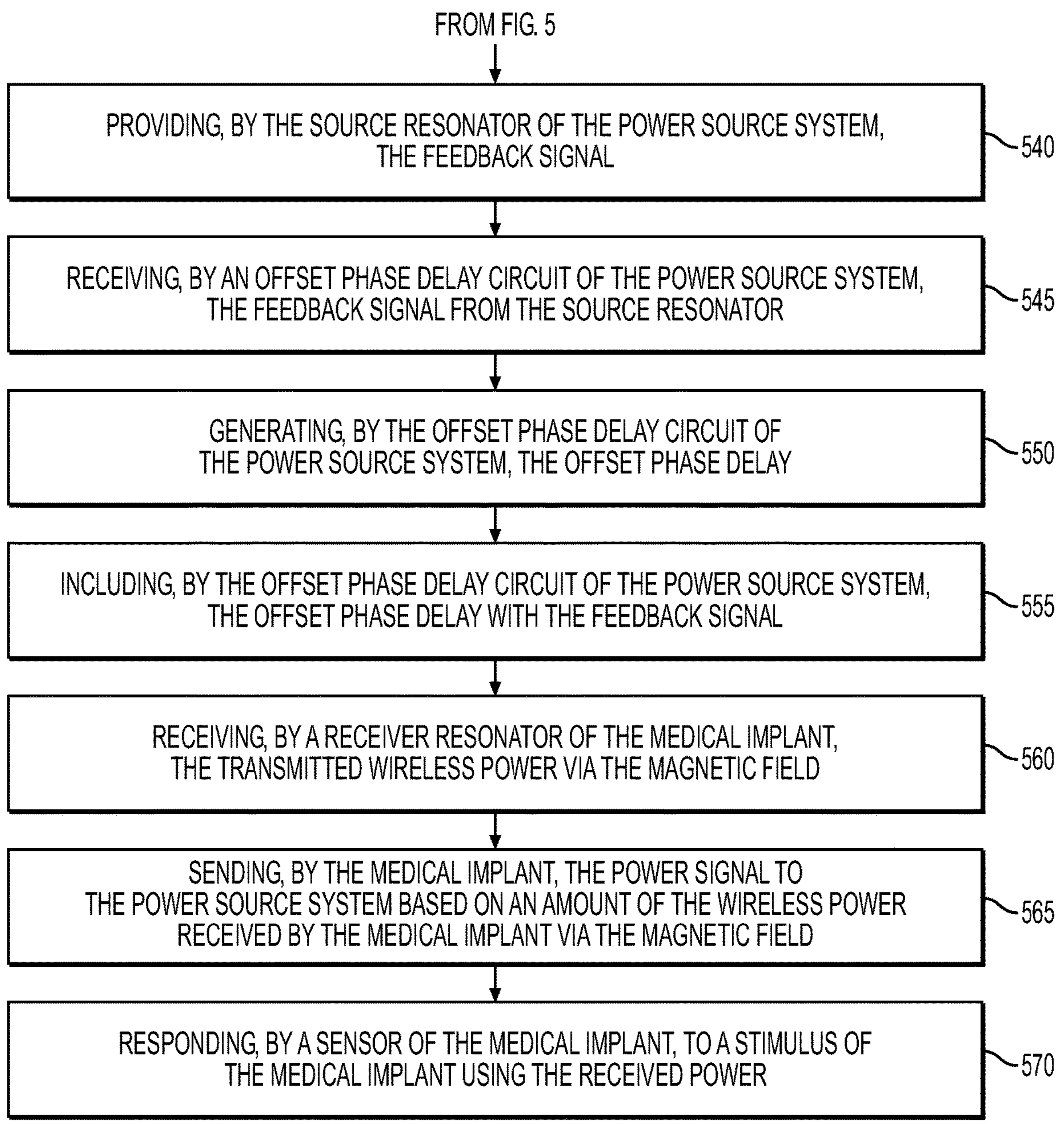

FIG. 5 depicts a flowchart of a method for wireless power transfer using the exemplary system of FIG. 1. Method 500 may control a transmission of wireless power from a source transmitter 106 of a power source system 100 to a medical implant 200. Method 500 may include controlling, by a source controller 104 of the source transmitter 106, input power based on a threshold and a power signal received from the medical implant 200 to limit the power received by the medical implant 200 (operation 505). Method 500 may include receiving, by an automatic gain controller 120 of the source transmitter 106, the input power (operation 510). Method 500 may include automatically adjusting, by the automatic gain controller 120 of the source transmitter 106, the input power based on a feedback signal with an offset phase delay signal (operation 515). Method 500 may include increasing, by the automatic gain controller 120, a signal-to-noise ratio of the feedback signal with the offset phase delay and decreasing (or limiting), by the automatic gain controller 120 a phase shift of a switching signal (operation 520). Method 500 may include providing, by the automatic gain controller 120 of the source transmitter 106, the adjusted input power as output power (operation 525). Method 500 may include limiting, by a switch protector 144 of a source resonator 140 of the source transmitter 106, power to a switch 142 of the source resonator 140 (operation 530). Method 500 may include generating, by the source resonator 140 including the switch 142, based on the output power, a magnetic field to transmit the wireless power via the magnetic field (operation 535). Method 500 may include providing, by the source resonator 140 of the source transmitter 106, the feedback signal (operation 540). Method 500 may include receiving, by an offset phase delay circuit 130 of the source transmitter 106, the feedback signal from the source resonator 140 (operation 545). Method 500 may include generating, by the offset phase delay circuit 130 of the source transmitter 106, the offset phase delay (operation 550). Method 500 may include including, by the offset phase delay circuit 130 of the source transmitter 106, the offset phase delay with the feedback signal (operation 555). Method 500 may include receiving, by an implant resonator 270 of the medical implant 200, the transmitted wireless power via the magnetic field (operation 560). Method 500 may include sending, by the medical implant 200, the power signal to the source transmitter 106 based on an amount of the wireless power received by the medical implant 200 via the magnetic field (operation 565). Method 500 may include responding, by one or more sensors 216 of the medical implant 200, to a stimulus of the medical implant 200 using the received power (operation 570). The feedback signal may be based on inductive coupling of the magnetic field between the source resonator 140 and the implant resonator 270.

As shown in the embodiments above, an advantage to the disclosed systems and methods is a constant wireless power transfer efficiency for a wide range of transfer distances without the need for external tuning. The disclosed systems and methods discussed above may reduce electromagnetic field exposure to a patient, reduce a potential temperature rise of an implant in a body of a patient, reduce a power supply volume and/or weight of the power source system, reduce electronic component temperature rise of the power source system and medical implant, and reduce an implant charging time.

Other embodiments of the disclosure will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A wirelessly powered medical implant system comprising:

a power source system including:

an automatic gain controller to receive input power, automatically adjust the input power based on a feedback signal with an offset phase delay, and provide the adjusted input power as output power;

a source resonator to generate, based on the output power, a magnetic field to transmit wireless power via the magnetic field, and provide the feedback signal; and an offset phase delay circuit to receive the feedback signal from the source resonator, generate the offset phase delay, and include the offset phase delay with the feedback signal, wherein the automatic gain controller is configured to increase a signal-to-noise ratio of the feedback signal with the offset phase delay from the offset phase delay circuit and decrease a phase shift of a switching signal to the source resonator; and a medical implant including:

an implant resonator to receive the transmitted wireless power via the magnetic field; and one or more sensors to respond to a stimulus of the medical implant using the received power, wherein the feedback signal is based on inductive coupling of the magnetic field between the source resonator and the implant resonator.

2. The system of claim 1, wherein the automatic gain controller includes:

a variable gain amplifier including an input electrically connected to an output of the offset phase delay circuit to receive the feedback signal with the offset phase delay.

3. The system of claim 2, wherein the automatic gain controller further includes:

a second stage amplifier including an input electrically connected to an output of the variable gain amplifier, and an output to provide the switching signal to the source resonator.

4. The system of claim 3, wherein the automatic gain controller further includes:

a feedback integrator including an input electrically connected to an output of the second stage amplifier, and an output to provide a signal to the variable gain amplifier.

5. The system of claim 3, wherein the automatic gain controller further includes:

a servo integrator including an input electrically connected to an output of the second stage amplifier, and an output to provide a signal to the variable gain amplifier.

6. The system of claim 1, wherein the automatic gain controller automatically adjusts the input power based on the feedback signal with the offset phase delay using parity time symmetry, and wherein the feedback signal is a coupling rate between the source resonator and the implant resonator.

7. The system of claim 1, wherein the offset phase delay circuit includes a resistor and capacitor in parallel to generate the offset phase delay.

8. The system of claim 1, wherein the medical implant is a knee implant, and the stimulus to the one or more sensors is one or more of a location or a magnitude of a load, or a change in the same of the one or more sensors of the knee implant.

9. A wirelessly powered medical implant system comprising:

a power source system including:

an automatic gain controller to receive input power, automatically adjust the input power based on a feedback signal with an offset phase delay, and provide the adjusted input power as output power;

a source resonator to generate, based on the output power, a magnetic field to transmit wireless power via the magnetic field, and provide the feedback signal;

an offset phase delay circuit to receive the feedback signal from the source resonator, generate the offset phase delay, and include the offset phase delay with the feedback signal; and a source controller to control the input power based on a power signal to limit the received power based on a threshold; and a medical implant including:

an implant resonator to receive the transmitted wireless power via the magnetic field; and one or more sensors to respond to a stimulus of the medical implant using the received power, wherein the feedback signal is based on inductive coupling of the magnetic field between the source resonator and the implant resonator.

10. The system of claim 9, wherein the power source system further includes a source transceiver to receive the power signal from the medical implant.

11. The system of claim 9, wherein the medical implant further includes:

an implant transceiver to send the power signal to the power source system based on an amount of the wireless power received by the medical implant via the magnetic field.

12. The system of claim 9, wherein the power signal provides information to the power source system that causes the source controller to control the input power to minimize heat in the medical implant due to excess wireless power received by the medical implant.

13. The system of claim 9, wherein the medical implant further includes an AC to DC rectifier to convert the received power to DC power.

14. The system of claim 9, wherein the medical implant is a knee implant, and the stimulus to the one or more sensors is one or more of a location or a magnitude of a load, or a change in the same of the one or more sensors of the knee implant.

15. A wirelessly powered medical implant system comprising:

a power source system including:

an automatic gain controller to receive input power, automatically adjust the input power based on a feedback signal with an offset phase delay, and provide the adjusted input power as output power;

a source resonator to generate, based on the output power, a magnetic field to transmit wireless power via the magnetic field, and provide the feedback signal, wherein the source resonator includes:

a resonant tank circuit, a switch to drive the resonant tank circuit, and a switch protector to limit power to the switch; and an offset phase delay circuit to receive the feedback signal from the source resonator, generate the offset phase delay, and include the offset phase delay with the feedback signal; and a medical implant including:

an implant resonator to receive the transmitted wireless power via the magnetic field; and one or more sensors to respond to a stimulus of the medical implant using the received power, wherein the feedback signal is based on inductive coupling of the magnetic field between the source resonator and the implant resonator.

16. The system of claim 15, wherein the source resonator further includes:

a driver comparator to receive the output power from the automatic gain controller, compare the output power with a power reference signal, and output a driver signal based on the comparison of the output power with the power reference signal.

17. The system of claim 16, wherein the switch protector includes:

a protection comparator to receive an output signal from the resonant tank circuit of the source resonator, compare the output signal with a protection reference signal, and output a switch protection signal based on the comparison of the output signal with the protection reference signal.

18. The system of claim 17, wherein the driver comparator receives the switch protection signal, and outputs the driver signal based on both (1) the comparison of the output power with the power reference signal, and (2) the protection reference signal.

19. The system of claim 17, wherein the driver comparator includes a latch input, and the switch protection signal is received by the latch input.

20. The system of claim 15, wherein the medical implant is a knee implant, and the stimulus to the one or more sensors is one or more of a location or a magnitude of a load, or a change in the same of the one or more sensors of the knee implant.

* * * * *